United States Patent
Fujimoto

(10) Patent No.: US 6,248,761 B1
(45) Date of Patent: Jun. 19, 2001

(54) PESTICIDAL COMPOSITIONS

(75) Inventor: Izumi Fujimoto, Minoo (JP)

(73) Assignee: Sumitomo Chemical Company, Limited

( * ) Notice: Subject to any disclaimer, the term of this patent is extended or adjusted under 35 U.S.C. 154(b) by 0 days.

(21) Appl. No.: 09/326,676

(22) Filed: Jun. 7, 1999

(30) Foreign Application Priority Data

Jun. 8, 1998 (JP) .................................................. 10-159261

(51) Int. Cl.⁷ ...................................................... A01N 43/40
(52) U.S. Cl. ................................................................. 514/345
(58) Field of Search .................................................. 514/345

(56) References Cited

FOREIGN PATENT DOCUMENTS 96 11909    4/1996   (WO) .

*Primary Examiner*—Allen J. Robinson
(74) *Attorney, Agent, or Firm*—Birch, Stewart, Kolasch & Birch, LLP

(57) ABSTRACT

Pesticidal compositions that effectively control pests which are harmful to materials comprising cellulose, i.e. timbers, veneers, engineering woods and paper are provided by the instant invention. The pesticidal composition of instant invention effectively controls pests which are harmful to materials comprising cellulose, by typically comprising an active ingredient of 3,5-dichloro-1-(3, 3-dichloro-2-propenyloxy)-4-[3-(5-trifluoromethylpyridin-2-yloxy) propyloxy]benzene and an inert carrier.

4 Claims, No Drawings

PESTICIDAL COMPOSITIONS

FIELD OF THE INVENTION

The instant invention relates to pesticidal compositions which control pests which are harmful to materials containing cellulose, and methods of controlling said pests.

BACKGROUND OF THE INVENTION

Pests which are harmful to materials containing cellulose, are usually known to tamper with materials containing cellulose, such as timbers, veneers, engineering woods, papers and the like. In this regard, structures which are produced from the materials containing cellulose (such as residential structures, historic structures and the like) are frequently affected by the pests in a negative manner. As an attempt to efficiently control pests which are harmful to materials containing cellulose, certain pesticidal compositions have contained chlordane as an active ingredient. However, sales of the pesticidal compositions containing chlordane have been halted, in view of a presumed long or short term harm that is introduced into the surrounding environment of where the provided pesticidal composition comprising chlordane is being utilized.

As a result, the pesticidal compositions attempting to control said pests have been swayed to otherwise comprise pesticidally alternative active ingredients that are distinct from chlordane when the objective of the pesticidal composition was to control pests which are harmful to materials containing cellulose, and that be commercially available for sales. Such commercially available pesticidal compositions have contained organophosphorous compounds such as chlorpyriphos, phoxim and fenitrothion; pyrethroid compounds such as permethrin, bifenthrin, silafluofen, cypermethrin, acrinathrin and tralomethrin; and neonicotinoid compounds such as imidacloprid, in order to control pests which are harmful to materials containing cellulose. Even if so, the pesticidal compositions containing such alternative active ingredients have failed to be thoroughly advantageous in controlling pests which are harmful to materials containing cellulose.

SUMMARY OF THE INVENTION

The instant invention provides for pesticidal compositions that control pests which are harmful to materials containing cellulose, and methods of controlling said pests. In this regard, such pesticidal compositions are advantageous in that the pesticidal composition of the instant invention can typically control said pests at a low dosage. Such pesticidal compositions are also advantageous in that the provided pesticidal composition can provide a residual effect, which would control said pests for an extended amount of time. Further, such pesticidal compositions are also advantageous in that said pesticidal compositions control pests which are harmful to materials containing cellulose without introducing a notable amount of harm to the surrounding environment of which the provided pesticidal composition is being utilized.

In order to meet the objectives of the instant invention, a pesticidal composition of the instant invention comprises 3,5-dichloro-1-(3,3-dichloro-2-propenyloxy)-4-[3-(5-trifluoromethylpyridin-2-yloxy) propyloxy] benzene and an inert carrier, and a method of the instant invention comprises utilizing the active ingredient compound of said pesticidal compositions.

DETAILED DESCRIPTION OF THE INVENTION

A pesticidal composition of the instant invention comprises 3,5-dichloro-1-(3,3-dichloro-2-propenyloxy)-4-[3-(5-trifluoromethylpyridin-2-yloxy) propyloxy]benzene as an active ingredient, in order to control pests which are harmful to materials containing cellulose. A method to produce the instant active ingredient is disclosed in Japanese unexamined patent 9-151172. The pesticidal compositions of the instant invention comprise the instant active ingredient in an amount that effectively controls pests which are harmful to materials containing cellulose, and in an amount which also depends on the formulation of the inventive pesticidal composition or the method in which the inventive pesticidal composition is being used. As such, the amount of the instant active ingredient which effectively controls pests in a typical pesticidal composition of the instant invention is preferably in an amount of from about 0.001% to 99% by weight, and is more preferably in an amount of from about 0.01% to 50% by weight, but is not limited thereto.

The pesticidal compositions of the instant invention also typically comprise an inert carrier, in an amount in which the inert carrier can assist the instant active ingredient to be carried through a process or method of controlling pests which are harmful to materials containing cellulose. As such an amount of the inert carrier, the inventive pesticidal compositions preferably comprise the inert carrier in an amount of from about 10% to 99.9%, provided that such a carrier is a solid, liquid or gas carrier, or a combination thereof. In such a case, examples of the solid carriers that may be in the pesticidal compositions of the instant invention include clays such as kaolin, diatomaceous earth, bentonite, fubasami clay and terra alba, synthetic hydrated silicon oxides, talc, ceramics, other inorganic minerals which are useful in producing formulated compositions such as sericite, quartz, sulfur, active carbons and calcium carbonate, chemical fertilizers such as ammonium sulfate, ammonium phosphate, ammonium nitrate, urea and ammonium chloride, and the like, as well as powders thereof, granules thereof, and a mixture thereof; examples of the liquid carriers that may be in the pesticidal compositions of the instant invention include water, alcohols such as methanol and ethanol, aromatic hydrocarbons such as toluene, xylene, ethylbenzene and methyl naphthalene, non-aromatic hydrocarbons such as hexane, cyclohexane, kerosene and light oils, esters such as ethyl acetate and butyl acetate, nitrites such as acetonitrile and isobutylonitrile, ethers such as diisopropyl ether and dioxane, amides such as N,N-dimethylformamide and N,N-dimethylacetamide, halogenated hydrocarbons such as dichloromethane, trichloroethane and carbon tetrachloride, dimethylsulfoxide, botanical oils such as soy oil and cotton seed oil, and the like, and a mixture thereof; and examples of the gas carriers that may be in the pesticidal compositions of the instant invention include propellants such as butane gas, liquid petroleum gas, dimethyl ether, carbonated gas, and the like, and a mixture thereof.

Further, the pesticidal compositions of the instant invention may additionally contain a coloring agent, a formulation auxiliary, or a combination thereof. As such, examples of such coloring agents that may be utilized in the pesticidal compositions of the instant invention include inorganic pigments such as metal oxides, titanium oxides and Prussian blue, organic dyes such as alizarine dyes, azo dyes and metallic phthalocyanine dyes, iron, manganese, boron, copper, cobalt, molybdenum, zinc and salts thereof, and the like, or a mixture thereof; and examples of such formulation auxiliaries that may be utilized in the pesticidal compositions of the instant invention include attaching and/or dispersing agents, surfactants, stabilizers, and the like, or a mixture thereof.

In the event that the attaching and/or dispersing agents are selected to be utilized as said formulation auxiliary in the pesticidal compositions of the instant invention, the attaching and/or dispersing agents are typically agents that help evenly disperse certain particles which are present in the inventive pesticidal compositions, help adhere the provided pesticidal composition to locations which the pesticidal composition is utilized upon, or a combination thereof. Exemplarily of such an attaching and/or dispersing agent that may be utilized in the inventive pesticidal compositions include caseins, gelatins, sugars such as starch, gum arabic, cellulose derivatives and alginic acids, lignin derivatives, betonite, synthetic water-soluble polymers such as polyvinyl alcohol, polyvinylpyrrolidone and polyacrylic acid, and the like, or a mixture thereof.

Examples of the surfactants that may be utilized as the formulation auxiliary in the pesticidal compositions of the instant invention include polyoxyethylenated alkyl sulfate esters, polyoxyethylenated alkyl sulfonate salts, alkylaryl sulfonate salts (for example, dodecylbenzenesulfonate and decylbenzenesulfonate), alkyl aryl ethers and polyoxyethylenated derivatives thereof, polyethyleneglycol ethers, higher alcohol esters, sugar alcohol derivatives, and the like, or a mixture thereof.

Examples of the stabilizers that may be utilized as a formulation auxiliary in the pesticidal compositions of the instant invention include PAP (acidic isopropyl phosphates), BHT (2,6-di-tert-butyl-4-methylphenol), BHA (2-tert-butyl4-methoxyphenol and 3-tert-butyl-4-methoxyphenol), botanical oils, mineral oils, fatty acids or esters thereof, and the like, or a mixture thereof.

Furthermore, the inventive pesticidal compositions may optionally contain diluents, emulsifiers, solvents, organic binding agents, auxiliary solvents, application attaching agents, sticking agent, plasticizers, UV light-stabilizing agents or stabilization enhancing agents, dyes, coloring pigments, drying agents, preservatives, precipitation preventing agents, skin irritation preventing agents, and the like, or a mixture thereof, if so desired.

In this regard, the pesticidal compositions of the instant invention should be formulated into suitable formulations, with examples of such suitable formulations of the inventive pesticidal compositions including oil formulations, wettable powders, flowables such as suspensible or emulsifiable concentrates, dusts, foaming granules, pastes, granules, aerosols, microenpapsulations, heated vaporization agents, fogging agents, liquid carbon dioxide solutions, and the like, or a combination thereof.

Flowables of the instant invention, such as the suspensible or emulsifiable concentrates, can be produced by adding about 1% to 75% by weight of the instant active ingredient to an aqueous mixture. Preferably, the instant active ingredient is added to the aqueous mixture so that the instant active ingredient is distributed into small particles therein. Said aqueous mixture which is utilized in the flowables of the instant invention, typically contains 0.5% to 15% by weight of a suspension auxiliary, with examples of such suspension auxiliaries including protective colloids or materials that endow notable augmentations of thixotropic properties to the inventive pesticidal compositions. More specifically, examples of such protective colloids which may be contained in the aqueous mixtures that participate in formulating the flowable formulations of the inventive pesticidal compositions, include gelatin, casein, gum, cellulose ether, polyvinyl alcohol, and the like, or a mixture thereof; and examples of such materials that endow thixotropic properties and that are utilized in the flowable formulations of the inventive pesticidal compositions include bentonite, aluminum magnesium silicate, xanthane gum, polyacrylates, and the like, or a mixture thereof. In addition to such, said aqueous mixture which is utilized in a flowable pesticidal compositions of the instant invention, may optionally contain 10% or less of other well known auxiliaries which are useful in flowable formulations, such as anti-foaming agents, anti-rust agents, stabilizers, sticking agents, soaking aid agents, anti-freezing agents, preservatives, fungicides, and the like, or a mixture thereof However, the pesticidal compositions of the instant invention may replace said aqueous mixture with oils in which the instant active ingredient is difficult to dissolve therein, in order to produce the flowables of the instant invention.

In view of controlling pests which are harmful to materials containing cellulose with a greater residual effect, it is preferable to have the pesticidal compositions of the instant invention formulated as a microencapsulation. In this regard, microencapsulations of the instant invention can be produced by utilizing interfacial polymerization methods, In-Situ methods, phase separation methods, solvent evaporation method, spray drying methods, hot-melt methods, pan coating methods, or the like. For example, in the case that the interfacial polymerization method is utilized to formulate the inventive pesticidal compositions as a microencapsulation, the microencapsulations of the instant invention may be produced by adding about 1% to 50% by weight of the instant active ingredient and about 0.001% to 1% by weight of an oil-soluble monomer which is useful to form a wall of a microencapsulation, to a mixture containing water and about 0.001% to 1% by weight of a water-soluble monomer that also can be useful to form a wall of a microencapsulation, and thereafter, reacting the achieved mixture for a duration of about 1 to 48 hours and at a temperature of about 30° C. to 80° C. Exemplarily of the components which maybe used to form the wall in a microencapsulation of the instant invention when using the interfacial polymerization methods, include the oil-soluble and water-soluble monomers, and more specifically, examples of said monomers include, a polybasic acid halide as the oil soluble monomers, a polyamide utilizing a polyamine as the water-soluble monomer, or using a polybasic acid halide as the oil soluble monomer, a polyester utilizing a polyphenol as the water-soluble monomer, using a polyisocyanate as the oil-soluble monomer, a polyurethane utilizing polyol as the water-soluble monomer, and the like. Further, the interfacial polymerization method may also produce microencapsulations of the instant invention by additionally comprising an optional step of dissolving said instant active ingredient and said oil-soluble monomer in an organic solvent previous to dissolving the instant active ingredient in said mixture, and/or an optional step of adding a suspension auxiliary or other auxiliaries useful in microencapsulations after reacting said achieved mixture. As such, examples of the other auxiliaries useful in microencapsulations include anti-foaming agents, anti-rust agents, stabilizers, sticking agents, soaking aid agents, anti-freezing agents, preservatives, fungicides and the like.

In the event a pesticidal composition of the instant invention is formulated as the heated vaporization agents, a heated vaporization agent of the instant invention may additionally comprise a component for combustion, an exothermic chemical reaction, or the like, or a combination thereof, in order to generate heat for the provided heated vaporization agent. Examples of such components for combustion that may be utilized in the heated vaporization agents of the instant invention include heat generating combustion agents such as nitrate salts, zinc nitrate salts, guanidine salts, potassium chlorate, nitrocellulose, ethylcellulose and wooden dusts, pyrolysis promoting agents such as alkali metal salts, dichromate and chromate, oxygen supplying agents such as potassium nitrate, combustion supporting agents such as melamine and wheat starch, dust diluents such as diatomaceous earth, binding agents such as synthetic pastes, and the like. Examples of such components for an exothermic reaction that may be utilized in the heated vaporization agents of the instant invention include chemically heat generating agents such as sulfides, polysulfides and hydrosulfides of alkali metals, hydrated salts and calcium oxides, catalysis agents such as carbon materials that are useful in notably altering the velocity of a reaction, carbon metals and terra alba, organic foaming agents such as azodicarbonimide, benzenesulfonyl hydrazide, dinitrosopentamethylenetetramine, polystyrene and polyurethane, and fillers such as segments of natural fibers, and the like.

Methods of controlling pests which are harmful to materials containing cellulose typically comprise utilizing 3,5-dichloro-1-(3,3-dichloro-2-propenyloxy)-4-[3-(5-trifluoromethylpyridin-2-yloxy) propyloxy]benzene on said pests or otherwise to the habitats of said pests, with examples of utilizing the pesticidal composition including injecting under a vacuum suction, applying, dispersing, soaking, mixing or the like, or a combination thereof to said pests or habitats of said pests. Preferably, the methods of the instant invention utilize the inventive pesticidal compositions by additionally diluting the provided pesticidal composition previous to utilizing the provided pesticidal composition. In such cases, the provided inventive pesticidal composition is typically diluted to a concentration of from about 0.001% to 99% by weight, and more preferably of from about 0.01% to 10% by weight. Under typical conditions, about 0.001 g to 500 g of the instant active ingredient may be utilized to control 1 $m^2$ of the location which said pesticidal composition is attempting to control.

For example, a method of the instant invention may entail mixing the instant active ingredient into an adhesive agent, utilizing the achieved adhesive agent to produce a product such as a particle board, and thereafter deploying the produced product in the habitat of pests which are harmful to materials comprising cellulose.

Exemplarily of such habitats of pests which are harmful to materials containing cellulose, include wood materials, soils, or other locations which are vulnerable to pests, and more specific examples of habitats include the components of houses which are produced from materials comprising cellulose, structures of residences or soils, or the like, or a combination thereof.

The pests which are controlled by utilizing the pesticidal compositions of the instant invention typically include pests that have a partiality to affect materials that comprise cellulose, with examples of the materials comprising cellulose including timbers, veneers, papers, engineering boards such as particle board, fiber board, wafer board, compilation compositions, strand boards, LVL, OSL, OSB, flake boards, and the like, or a combination thereof. In this regard, the pests which are harmful to materials containing cellulose typically include termites (Isoptera), beetles (Coleoptera), ants or bees or sawflies or wasps (Hymenoptera), and the like. Examples of such termites (Isoptera) include Mastotermitidae, Termopsidae such as Zootermopsis, Archotermopsis, Hodotermopsis, Porotetermes and Stolotermes, Kalotermidae such as Kalotemes, Neotermes, Cryptotermes, Incisitermes and Glyptotermes, Hodotermitidae such as Hodotermes, Microhodotermnes and Anacanthotermes, Rhinotermitidae such as Reticulitermes, Heterotermes, Coptotermes and Schedolinotermes, Serritermitidae, Termitidae such as Amitermes, Drepanotermes, Hopitalitermes, Trinervitermes, Macrotermes, Nasutitermes, Percapritermes and Anoplotermes; examples of such beetles (Coleoptera) include bark beetles (Scolytidae) such as Xyleborus and Scolytoplatypus, longicom beetles (Cerambycidae) such as Monochamus, Hylotrupes, Hesperophanus, Chlorophorus, Palaeocallidium, Semanotus, Purpuricenus and Stromatium, Rynchophoridae such as Sipalinus, Platypodidae (platypodids) such as Crossotarsus and Platypus, powder-post beetles (Lyctidae) such as Lyctus, false powderpost beetles (Bostrychidae) such as Dinoderus, Bostrychus and Sinoderus, deathwatch beetles (Anobiidae) such as Emobius, Anobium, Xyletinus, Xestobium, Ptilinus, Nicobium and Ptilineurus, and Buprestidae; examples of such ants, bees, sawflies or wasps (Hymenoptera) include homtails (Siricidae) such as Urocerus and Sirex, and the like. As such, more specific examples of the above termites (Isoptera) that are generally controlled by the inventive pesticidal compositions include *Reticulitermes speratus, Coptotermesformosanus, Incisitermes minor, Cryptotermes domesticus, Odontotermesformosanus, Neotermes koshunensis, Glyptotermes satsumensis, Glyptotermes nakajimai, Glyptotermesfuscus, Glyptotermes kodamai, Glyptotermes kushimensis, Hodotermopsisjaponica, Coptotermes guangzhoensis, Reticulitermes miyatakei, Reticulitermesflaviceps amamianus*, Reticulitermes sp., *Nasutitermes takasagoensis, Pericapriterme nitobei* and *Sinocapriternes mushae*, and the like.

In addition, the pesticidal compositions of the instant invention may optionally comprise other well known pesticidally active compounds which are known to posses pesticidal effects when used on pests which are harmful to materials containing cellulose. In such cases that the inventive pesticidal compositions additionally contain such compounds, said compositions can enhance the pesticidal activity against pests which are harmful to materials containing cellulose.

If so desired, the pesticidal compositions of the instant invention may also optionally comprise fungicidal compounds, so that the inventive pesticidal compositions may additionally have a control over fungi, bacteria, algae and the like. Exemplarily of the fungicidal compounds that may be utilized in the pesticidal compositions of the instant invention include Trihalosulfonyl compounds such as dichlofluanid, tolyfluanid, folpet, fluorfolpet, and fungicidally active isomers thereof; Iodine compounds such as IPBC, amical 48, IF 1000, EBI, and fungicidally active isomers thereof; Phenol compounds such as PCP-laurate, DCBP, tribromophenol, and fungicidally active isomers thereof; azole compounds such as fenarimol, flurprimidol, fluotrimazole, triadimefon, triadimenol, diclobutrazol, paclobutrazole, diniconazole, uniconazole, triflumizole, flutriafol, flusilazole, penconazole, prochloraz, triarimol, fenarimol, bitertanol, imazalil, etaconazole, fenapanil, viniconazole, difenoconazole, bromuconazole, myclobutanil, hexaconazole, furconazole-cis, fenethanil, tebuconazole, propiconazole, azaconazole, cyproconazole, and fungicidally active isomers thereof; carbamate compounds such as zineb, maneb, benomyl, thiophanate-methyl, cypendazole, carbendazime, prothiocarb, diethofencarb, and fungicidally active isomers thereof; antibiotic compounds such as validamycin A, kasugamycin, milbrmycin, and fungicidally active isomers thereof; anilide compounds such as mepronil, flutolanil, pencycuron, carboxin, oxycarboxin, pyracarbolid, mebenil, furcarbanil, cyclafuramid, benodanil, glanobax, metalaxyl, ofurace, benalaxyl, oxadixyl, cyprofuram, clordinacon, metasulfovax, tecloftalam, and fungicidally active isomers thereof; organophosphorus compounds such as edifenphos, IBP, pyrazophos, Alliette, tolclofos-methyl, and fungicidally active isomers thereof; dicarboxyimide compounds such as dichlozoline, iprodione, vinclozolin, procymidone, myclozolin, fluoroimide, and fungicidally active isomers thereof; tin compounds such as tributyltin octylate, tributyltin oleate, bis-tributyltin oxide, tributyltin naphthalate, tributyltin phosphate, tributyltin benzoate, and fungicidally active isomers thereof; thiocyanate compounds such as methylene bisthiocyanate, 2-thiocyanomethylthiobenzothiazole, and fungicidally active isomers thereof; quaternary ammonium compounds such as benzyldimethyltetradecylammonium chloride and benzyldimethyldodecylammonium chloride, and fungicidally active isomers thereof; benzimidazole compounds such as fuberidazole, BCM, thiabendazole, benomyl, and fungicidally active isomers thereof; morphline compounds such as tridemorf, pyridine compounds, and fungicidally active isomers thereof; naphthenic acid compounds such as zinc naphthate, copper naphthate, quinone compounds, and fungicidally active isomers thereof; boron compounds such as boric acid, borax, boric acid salts, and fungicidally active isomers thereof; urea compounds, ftiran derivatives, curmecyclox, Isothiazolinone compounds, N-cyclohexyl diaziniumdioxy compounds, and fungicidally active isomers thereof; and the like, or a mixture thereof.

In the event the pesticidal compositions of the instant invention also optionally contain a fungicide to provide a control over bacteria, examples of the bacteria that are controlled by the pesticidal compositions of the instant invention include Bacteria that change the color of wood, Bacteria that decompose wood, and the like. More specifically, examples of such bacteria that change the color of wood include Ascomycetes such as Caratocystis, Deuteromycetes such as Aspergillus, Aubeobasidium, Dactyleum, Penicillium, Aclerophoma, Scopularia and Tricoderma, Zygomycetes such as Mucor, and the like. In addition, examples of such Bacteria that decompose wood include Ascomycetes such as Chaetomium, Chetonium, Humicola, Petriella and Trichurus, Basidiomycetes such as Coniophera, Coriolus, Donbiopora, Glenospora, Gloeophyllum, Lentinus, Paxillus, Pleurotus, Poria, Serpula and Tyromyces, and Deuteromycetes such as Cladosporium, and the like.

EXAMPLES

Hereinafter, the following examples are set forth as an aid to those desiring to practice the instant invention, and are not to be limiting to the instant invention in anyway.

Formulation Example 1

Solvesso 150 (hydrocarbon solvent produced by Exxon Corp.) is added to a mixture comprising 100 g of the instant active ingredient, 20 g of dodecylbenzene sulfonate and 80 g of decylbenzene sulfonate, so that the achieved mixture amounts to 1000 mL. Thereafter, the achieved mixture is uniformly mixed to result an emulsion which comprises the instant active ingredient at a concentration of 10 g per liter of said emulsion.

Formulation Example 2

Five grams (5 g) of Sorpol (surfactant produced by Toho Chemical) is added to a mixture comprising 50 g of the instant active ingredient and 45 g of xylene, and is then uniformly mixed, to obtain an emulsion comprising the instant active ingredient at a concentration of 50 g per liter of said emulsion.

Formulation Example 3

A hundred grams (100 g) of the instant compound, 4.8 g of sumidur L-75 (polyisocyanate produced by Sumitomo-Bayer Urethane) and 100 g of Solvesso 200 (hydrocarbon solvent produced by Exxon Corp.) are uniformly mixed. The achieved mixture is then added to 175 g of an aqueous solution that comprises 10% by weight of gum arabic and 6 g of ethylene glycol, and is then agitated and dispersed at 3500 rpm at room temperature by use of a T.K. Auto-homomixer (homoginizer produced by Tokushukika Kogyo), in order to obtain small droplets in the mixture. A microencapsulated slurry is then obtained by gently agitating the achieved mixture for 24 hours at 60° C. Six hundred fourteen and one-fifth grams (614.2 g) of an aqueous solution containing 2 g of xanthan gum and 4 g of aluminum silicate is added to the achieved slurry, to produce a microencapsulatied formulation of the instant invention.

Formulation Example 4

One tenth gram (0.1 g) of the instant active ingredient and 1 g of IPBC is added to an organic solution, and was uniformly mixed to amount to 100 mL, in order to obtain a oil formulation that comprises the instant active ingredient at a concentration of 0.1 g per 1 L of the provided formulation.

Test Example 1

A 10 mL emulsion according to Formulation Example 2 was formulated and then diluted to an appropriate concentration, to achieve a diluted aqueous emulsion. The diluted emulsion was mixed with 200 g of soil, so that the concentration of the instant active ingredient in the achieved mixture of soil was 250 ppm. The achieved mixture of soil was then maintained in darkness at a temperature of 40° C. After a time period set forth in Table 1, three samples consisting of 10 g of the mixture of soil, was then transferred into a corresponding plastic chalet which had a diameter of 9 cm. Each sample then had water added, and had 10 Formosan subterranean termites (*Coptotermes formosanus*) deposited thereto. Ten days after depositing the termites to the plastic challet, the mortality rate was determined by examining for mortal termites. For each given period of time set forth in Table 1, the average mortality rate of the Formosan subterranean termites was calculated and is given in Table 1.

TABLE 1

| | Time the Mixture of Soil was Maintained in Darkness | |
|---|---|---|
| | Initial* | 1 Year |
| Mortality Rate (%) | 95 | 100 |

*Not maintained in darkness

Test Example 2

Ten (10) worker Formosan subterranean termites (*Coptotermes formosanus*) were deposited into a plastic chalet which had a diameter of 9 cm. An emulsion according to Formulation Example 2 was then prepared and diluted to a concentration of 1% by weight, in order to result a diluted aqueous emulsion. Six milliliters (6 mL) of the achieve diluted aqueous emulsion were then sprayed onto the Formosan subterranean termites from a distance of about 60 cm, and the sprayed Formosan subterranean termites were then transferred to another chalet. The mortality rate of the Formosan subterranean termites was examined after a duration of time set forth in Table 2. The test was repeated three times and the averages of the resulting mortality rates are given in Table 2.

TABLE 2

| | Elapsed Time After the Spraying | |
|---|---|---|
| | 1 day | 3 days |
| Mortality Rate (%) | 86.7 | 100 |

Test Example 3

Three formulations of the inventive pesticidal composition were prepared, dissolved in acetone, and applied to a half of each corresponding piece of filter paper which had a diameter of 33 mm. After the filter papers were allowed to dry, the achieved filter papers were placed in plastic chalets which had a diameter of 35 mm, to obtain each test container. Subsequently, water was dropped onto the filter papers in the plastic chalets so that the resulting concentration of the instant active ingredient in the filter papers were about 0.1% by weight. Ten (10) worker Formosan subterranean termites (*Coptotermes formosanus*) and 10 *Reticulitermes speratus* were deposited into each test container, and the mortality rate was examined after an elapsed amount of time set forth in Table 3. The test was repeated three times and the averages of the resulting mortality rates are set forth in Table 3.

TABLE 3

| | Elapsed Time | | |
|---|---|---|---|
| Mortality rate (%) of: | 1 day | 3 days | 5 days |
| Formosan subterranean termites | 16.7 | 100 | |
| *Reticulitermes speratus* | 0 | 90 | 100 |

The results from the above test examples evidence that unexpected and advantageous properties are possessed by the inventive pesticidal compositions by providing an effective control over pests which are harmful to materials containing cellulose.

What is claimed is:

1. A method of controlling termites, said method comprising:
    applying to termites or a location inhabited by termites, an effective amount of 3,5-dichloro-1-(3,3-dichloro-2-propenyloxy)-4-[3-(5-trifluoromethylpyridin-2-yloxy)propyloxy]benzene.

2. The method according to claim 1, said method comprising:
    applying to a soil an effective amount of 3,5-dichloro-1-(3,3-dichloro-2-propenyloxy)-4-[3-(5-trifluoromethylpyridin-2-yloxy)propyloxy]benzene.

3. The method according to claim 1, wherein the effective amount is 0.001 g to 500 g per 1 m$^2$.

4. The method according to claim 2, wherein the effective amount is 0.001 g to 500 g per 1 m$^2$.

* * * * *